United States Patent [19]

van Andel

[11] Patent Number: Plant 6,290

[45] Date of Patent: Sep. 13, 1988

[54] CARNATION NAMED STACOR

[75] Inventor: Jacob van Andel, Aalsmeer, Netherlands

[73] Assignee: Van Staaveren B.V., Aalsmeer, Netherlands

[21] Appl. No.: 912,803

[22] Filed: Sep. 29, 1986

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new carnation cultivar particularly distinguished by the solid light pink coloration of its medium sized, rather dense and almost ball-shaped blooms which are borne on long, strong, straight stems on a plant which blooms profusely and continuously with a vigorous, upgrowth habit with moderately abundant foliage, the plant height averaging about 100 to 150 cm., thereby providing extra long flower stems which have a particular advantage for the cut flower market.

1 Drawing Sheet

BACKGROUND OF THE NEW PLANT

This new carnation cultivar is the result of breeding efforts carried on by me at Aalsmeer, Holland, with the object of producing plants of new flower color, this particular plant originating as a seedling resulting from my crossing of selected and individually identified plants growing among a stock of plants maintained at Aalsmeer for breeding purposes. This particular seedling was selected by me for propagation and test because of its relatively dense, almost ball-shaped flower of a lovely light pink coloration borne on long, strong stems and its apparently very favorable growth habit. This selected plant was reproduced under my direction at Aalsmeer by means of cuttings of the parent and the result of that propagation appearing to be very favorable with respect to retention of the novel characteristics of the parent, asexual propagation was continued through several successive generations, which established that the novel and distinctive characteristics of this selected plant appeared to be firmly fixed and were fully retained from generation to generation.

DESCRIPTION OF THE DRAWING

This new carnation cultivar is illustrated by the accompanying photographic drawing which shows, in full color, a face view of a typical flower illustrating the dense character of its mass of petals and its solid overall coloration, the color shown being as nearly true to that specified herein as is reasonably possible to obtain by conventional photographic procedures.

DESCRIPTION OF THE NEW PLANT

The following is a detailed description of my new carnation cultivar based upon observations of greenhouse grown plants made at Aalsmeer, Holland, the color designations being specified according to the the R.H.S. Colour Chart published by The Royal Horticultural Society at London, England.

THE PLANT

Origin: Seedling.

Parentage:

*Seed parent.*—"Lontarion".

*Pollen parent.*—An unnamed stock carnation plant identified by No. 81011-1C in breeding records maintained at my nursery at Aalsmeer, Holland.

Classification:

*Botanic.*—Hybrid *Dianthus caryophyllus.*

*Commercial.*—Standard carnation.

Form: Tall, erect bush.

Height: Averaging to 150 cm.

Growth rate: Very fast.

Main stem length: About 120 cm.

Branching character: Normal.

Growth habit: Vigorous, strong and upright.

Foliage:

*Quantity.*—Moderately abundant, depending on season.

*Leaf size.*—Averaging about 18 cm. long and about 0.8 cm. wide.

*Shape.*—Linear with acuminate apex, entire margin and downwardly curled.

*Texture.*—Leathery.

*Color.*—Upper side and lower side, Grey/Green.

THE BUD

Form: Ovoid.

Size: Medium.

*Diameter.*—About 2 cm.

Color of petals:

*When sepals first divide.*—48D.

*When petals begin to unfurl.*—48D.

Sepals: The sepals are joined at the lower part and the upper part is of generally ovate form with a pointed apex. The sepals are hooded over the bud until they divide and when the flowers open, the sepals curl back.

Calyx:

*Shape.*—Cylindrical.

*Size.*—Medium.

*Splitting.*—The calyx rarely splits.

*Aspect.*—Smooth.

Flower stem:

*Length.*—About 120 cm.

*Character.*—Strong and erect.

*Color.*—Grey/Green.

THE FLOWER

Blooming habit: Continuous and profuse.

Size of bloom: Medium.

*Diameter.*—About 8.5 cm.

*Depth.*—About 3 cm.

Borne: Singly.

Shape:

*When bloom first opens.*—High centered.

*When bloom matures.*—Dome shaped.

Petalage:

*Number of petals.*—Very many, giving a very dense appearance.

*Arrangement.*—Imbricated. Form: Fan shaped with straight margins and undulant, deeply serrated outer ends.

*Texture.*—Soft.

*Appearance.*—Velvety.

*Color.*—All petals, 48D on both top and reverse sides, the base end being white and green.

Fragrance: None.

Persistence: The petals hang on and dry.

Lasting quality:

*As cut flower.*—At least ten days with vase keeping.

REPRODUCTIVE ORGANS

Stamens:

*Number.*—Very few.

*Arrangement.*—Around the ovary.

*Anthers.*—Color: White with a pink top.

*Filaments.*—Length: 0.5 to 3 cm. Color: White.

*Pollen.*—Color: Yellow/Brown.

Pistils:

*Number.*—One.

*Styles.*—Length: About 2 cm. Color: Light Pink.

*Stigmas.*—Color: White.

Character of ovary: Normal.

I claim:

1. The new and distinct carnation cultivar, substantially as herein shown and described, characterized by the uniform overall pink coloration of its medium sized, generally ball-shaped blooms which are carried on long, straight, stiff stems; and by its rapid growth habit and a moderately abundant production of foliage.

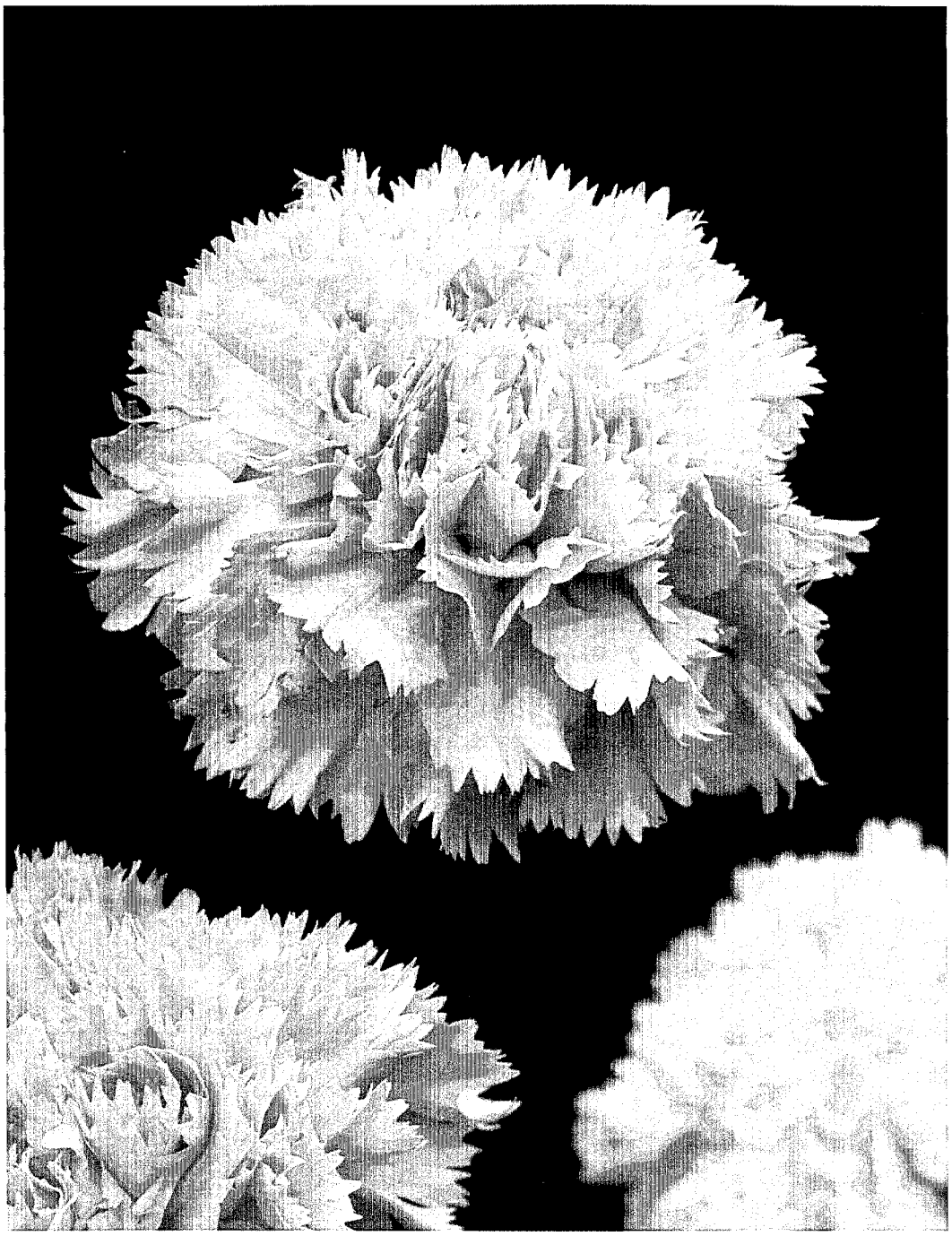

* * * * *